United States Patent
Lu et al.

(10) Patent No.: US 11,917,911 B2
(45) Date of Patent: Feb. 27, 2024

(54) SMALL-MOLECULE ELECTRON DONOR MATERIAL WITH AN ELECTRON-DEFICIENT HETEROCYCLIC CORE, PREPARATION AND APPLICATION THEREOF

(71) Applicants: Taizhou University, Taizhou (CN); Taizhou huimo technology co., ltd, Taizhou (CN)

(72) Inventors: Shirong Lu, Taizhou (CN); Liu Zhu, Taizhou (CN)

(73) Assignees: TAIZHOU UNIVERSITY, Taizhou (CN); TAIZHOU HUIMO TECHNOLOGY CO., LTD, Taizhou (CN)

( * ) Notice: Subject to any disclaimer, the term of this patent is extended or adjusted under 35 U.S.C. 154(b) by 0 days.

(21) Appl. No.: 18/098,757

(22) Filed: Jan. 19, 2023

(65) Prior Publication Data
US 2023/0397492 A1    Dec. 7, 2023

(30) Foreign Application Priority Data
Jun. 7, 2022    (CN) .......................... 202210639636.5

(51) Int. Cl.
*C07D 417/14*    (2006.01)
*H10K 85/60*    (2023.01)
*H10K 30/30*    (2023.01)

(52) U.S. Cl.
CPC ......... *H10K 85/655* (2023.02); *C07D 417/14* (2013.01); *H10K 85/656* (2023.02); *H10K 30/30* (2023.02)

(58) Field of Classification Search
CPC ................................................... C07D 417/14
See application file for complete search history.

(56) References Cited

FOREIGN PATENT DOCUMENTS

CN    111499624 A * 8/2020  ........... C07D 417/14

* cited by examiner

*Primary Examiner* — Khanh T Nguyen
(74) *Attorney, Agent, or Firm* — Stuart H. Mayer; Kaplan Breyer Schwarz LLP (57) ABSTRACT

Disclosed are a small-molecule electron donor material with an electron-deficient heterocyclic core, preparation and application thereof, belonging to technical field of solar cells. According to the present application, a brand-new electron-deficient heterocyclic unit which has never been applied to an organic solar cell is used as a core unit to prepare a small-molecule electron donor material with an A-D-A'-D-A skeleton structure, and the molecular structure of the small-molecule electron donor material is shown in formula (I).

8 Claims, 4 Drawing Sheets

SMALL-MOLECULE ELECTRON DONOR MATERIAL WITH AN ELECTRON-DEFICIENT HETEROCYCLIC CORE, PREPARATION AND APPLICATION THEREOF

CROSS-REFERENCE TO RELATED APPLICATIONS

This application claims priority to Chinese Patent Application No. 202210639636.5, filed on Jun. 7, 2022, the contents of which are hereby incorporated by reference.

TECHNICAL FIELD

The present application relates to the technical field of solar cells, and in particular to a small-molecule electron donor material with an electron-deficient heterocyclic core, its preparation and application.

BACKGROUND

Organic solar cell is flexible and printable solar cell consisting of organic semiconductor material as the core, and has the advantages of wide source of raw materials, good flexibility, solution processable and printable. It has become one of the hot spots for research in the industry in the past years, with photovoltaic conversion efficiency of all-small-molecule organic photovoltaic device with non-fullerene as the acceptor material exceeding 16 percent (%); yet, non-fullerene electron acceptor materials are expensive as comparing to acceptor materials of fullerenes, and organic solar cells prepared with non-fullerene system are sensitive to film thickness, unsuitable for large-area printing applications, and therefore difficult for marketing.

Small-molecule electron donor materials BTR, BTR-Cl, S1 and S2 based on benzodithiophene (BDT) core with good solubility and stability have been marketed, and the system composed of BTR and fullerene electron acceptor $PC_{71}BM$ has better photoelectric conversion efficiency, yet the efficiency obtained is far less than that of non-fullerene electron acceptor, mainly because the phase separation morphology of the active layer is not good enough, in addition to other disadvantages such as abundant synthesis process and expensive intermediate materials. The reported all-small-molecule organic photovoltaic devices based on oligothiophene small-molecule donor have a photovoltaic conversion efficiency of more than 15%, of which the materials have gradually received widespread attention because of the advantages of simple synthesis and low costs. Nevertheless, it is limited in the field of small-molecular electron donor materials by the single structure of oligothiophene and the scarcity of optimization sites as well as modifiable units, resulting in the scarcity of optimization strategies in structural design. Accordingly, a novel type of electron-deficient heterocyclic core unit material of A-D-A'-D-A type based on oligothiophene skeleton is expected to be developed, which has great scientific impact and practical significance in broadening the structure optimization strategy of oligothiophene system and developing new small-molecule electron donor materials.

SUMMARY

In view of the above-mentioned shortcomings of the prior art, the present application provides a small-molecule electron donor material with an electron-deficient heterocyclic core and its preparation and application, establishing a new structural optimization route for small-molecule electron donor materials based on oligothiophene skeletons through a new structural designing concept.

To achieve the above objectives and other related objectives, one of the aspects of the present application provides a small-molecule electron donor material with an electron-deficient heterocyclic core, including a molecular structure as shown in formula (I):

among them, R is any one of the following structures:

-continued

Optionally, the small-molecule electron donor material with an electron-deficient heterocyclic core has a molecular structure as follows:

The BTP-eC9-4F has a molecular structural formula as shown below:

Another aspect of the present application provides a photovoltaic device equipped with the small-molecule electron donor material with an electron-deficient heterocyclic core as described in one aspect of the present application or the active layer material as described in one aspect of the present application.

Another aspect of the present application provides an active layer material for photovoltaic devices, where the active layer material includes the small-molecule electron donor material with an electron-deficient heterocyclic core as described in one aspect of the present application.

Optionally, the active layer material also includes an electron acceptor material.

Optionally, the electron acceptor material includes, but is not limited to, $PC_{71}BM$, Y6, BTP-eC9-4F, CH1007, IDIC, and N3.

Optionally, the photovoltaic device sequentially includes: a substrate, a hole transport layer, an active layer, an electron transport layer, and a metal electrode.

Optionally, the substrate includes a transparent glass and a transparent conductive film.

Optionally, the hole transport layer is any one of PEDOT:PSS and $MoO_3$.

Optionally, the electron transport layer is any one selected from a group of Phe-NaDPO, PDINO and PFBr.

Optionally, the hole transport layer has a thickness in a range of 20-40 nanometers (nm), and specifically of 20 nm, 25 nm, 30 nm, 35 nm, and 40 nm, etc.

Optionally, the electron transport layer has a thickness in a range of 5-10 nm, and specifically of 5 nm, 6 nm, 7 nm, 8 nm, 9 nm, and 10 nm, etc.

Optionally, the active layer has a thickness in a range of 80-200 nm, and specifically of 80 nm, 100 nm, 110 nm, 120 nm, 140 nm, 160 nm, 180 nm, and 200 nm, etc.

Optionally, the metal electrode is any one of silver (Ag) and aluminum.

Optionally, the photovoltaic device is an all-small-molecule solar cell.

All small-molecule here indicates that both the donor material and acceptor material of the active layer are of small-molecule.

Another aspect of the present application provides an application of the small-molecule electron donor material with an electron-deficient heterocyclic core as described in one aspect of the present application or the active layer material as described in one aspect of the present application in preparing photovoltaic devices.

Another aspect of the present application provides a method for preparing the small-molecule electron donor material with an electron-deficient heterocyclic core, including: mixing raw materials and reacting to obtain the small-molecule electron donor material with an electron-deficient heterocyclic core, where the raw materials include dialdehyde compound and dicyanoethyl rhodanine, and the dialdehyde compound has a molecular structural formula as follows:

where R is any one of the following structures:

Optionally, R in the molecular structural formula of the dialdehyde compound is any one of the following structures:

Optionally, the method for preparing the small-molecule electron donor material with an electron-deficient heterocyclic core includes:

mixing the dialdehyde compound with solvent, dicyanoethyl rhodanine and catalyst, and reacting to obtain the small-molecule electron donor material.

Optionally, the method for preparing the small-molecule electron donor material with an electron-deficient heterocyclic core includes steps as follows:

(1) mixing dibromo electron-deficient heterocyclic unit (i.e. compound 1), solvent, octylthiophene tin reagent and catalyst, and reacting to obtain a compound 2;

(2) mixing the compound 2 with solvent and lithium diisopropylamide, reacting, adding alkyl tin chloride reagent for reaction under room temperature so as to obtain a compound 3 (i.e. a double tin reagent substitute of the compound 2);

(3) mixing the compound 3 (i.e. the double tin reagent substitute of the compound 2), with solvent, thiophene π-bridged aldehyde and catalyst, to react to obtain a dialdehyde compound (i.e. compound 4); and (4) mixing the dialdehyde compound with solvent, dicyanoethyl rhodanine and catalyst, and reacting to obtain the small-molecule electron donor material (compound 5);
the method follows a reaction route belows:

Optionally, the reacting in the step (1) is carried out under temperature of 100-200 degree Celsius (C) for a duration of 12-72 hours (h); the temperature includes 100° C., 105° C., 110° C., 115° C., 120° C., 125° C., 130° C., 135° C., 140° C., 145° C., 150° C., 155° C., 160° C., 165° C., 170° C., Optionally, the dibromo electron-deficient heterocyclic unit in step (1) is in a mole ratio of 1:(2.0-2.5) to the octylthiophene tin reagent.

Optionally, the dibromo electron-deficient heterocyclic unit in the step (1) is in a mole ratio of 1:(0.1-0.2) to the catalyst.

Optionally, the solvent in the step (1) includes, but not limited to, dioxane, toluene, chlorobenzene and o-xylene.

Optionally, the catalyst in the step (1) is at least one selected from a group of tetrakis(triphenylphosphine)palladium, tris(dibenzylideneacetone)dipalladium, and [1,1'-bis(diphenylphosphino)ferrocene]dichloropalladium(II).

175° C., 180° C., 200° C., etc.; and the duration of reaction includes 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 35 h, 40 h, 45 h, 50 h, 55 h, 60 h, 65 h, 70 h, and 72 h, and so on.

Optionally, the solvent is distilled off from a reaction solution under reduced pressure in step (1) after the reaction is finished, followed by separation by silica gel column chromatography to obtain the compound 2

Optionally, the separation by silica gel column chromatography in the step (1) adopts a chloroform/petroleum ether mixture as an eluent; and preferably, the chloroform/petroleum ether mixture includes chloroform and petroleum ether in a volume ratio of 1:6.

Optionally, the compound 2 is in a mole ratio of 1 (2.0-3.0) to lithium diisopropylamide in the step (2).

Optionally, the compound 2 is in a mole ratio of 1:(3.0-5.0) to alkyl tin chloride reagent in the step (2).

Optionally, the solvent includes but is not limited to tetrahydrofuran, 2-methyltetrahydrofuran, ether and toluene in the step (2).

Optionally, the alkyl tin chloride reagent includes but is not limited to trimethyltin chloride, triethyltin chloride, trinpropyltinchloride, chlorotributyltin and chloro(trioctyl) stannane in the step (2).

Optionally, in the step (2), the compound 2 and lithium diisopropylamide are reacted at temperature of −30° C.--100° C. for a duration of 0.5-2.5 h; specifically, the temperature can be −30° C., −35° C., −40° C., −45° C., −50° C., −55° C., −60° C., −65° C., −70° C., −75° C., −80° C., −85° C., −90° C., −95° C. and −100° C.; and specifically, the duration can be 0.5 h, 0.7 h, 0.9 h, 1.1 h, 1.3 h, 1.5 h, 1.7 h, 1.9 h, 2.1 h, 2.3 h, and 2.5 h, etc.

Optionally, in the step (2), the reaction under room temperature is carried out for a duration of 3-20 h, including but not limited to 3 h, 4 h, 5 h, 6 h, 7 h, 8 h, 9 h, 10 h, 11 h, 12 h, 13 h, 14 h, 15 h, 16 h, 17 h, 18 h, 19 h, 20 h.

Optionally, in the step (2), after the reaction is finished, the reaction is quenched, followed by extraction and drying, then the solvent is distilled off from a reaction solution under reduced pressure to obtain the compound 3; and preferably, the reaction is quenched by saturated potassium iodide aqueous solution, extracted with ethyl acetate, and dried with anhydrous magnesium sulfate.

Optionally, the compound 3 is in a mole ratio of 1:(2.0-2.5) to the thiophene π-bridged aldehyde in the step (3).

Optionally, the compound 3 is in a mole ratio of 1:(0.1-0.2) to the catalyst in the step (3).

Optionally, the solvent includes but is not limited to dioxane, toluene, chlorobenzene and o-xylene in the step (3).

Optionally, the catalyst the catalyst in the step (3) is at least one selected from a group of tetrakis(triphenylphosphine)palladium, tris(dibenzylideneacetone)dipalladium, and [1,1′-bis(diphenylphosphino)ferrocene]dichloropalladium(II).

Optionally, the reacting in the step (3) is carried out under temperature of 100-200° C. for a duration of 12-72 h; specifically, the temperature can be 100° C., 105° C., 110° C., 115° C., 120° C., 125° C., 130° C., 135° C., 140° C., 145° C., 150° C., 155° C., 160° C., 165° C., 170° C., 175° C., 180° C., and 200° C., etc.; and the duration can be 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 35 h, 40 h, 45 h, 50 h, 55 h, 60 h, 65 h, 70 h, and 72 h, and so on.

Optionally, the solvent is distilled off from a reaction solution under reduced pressure in step (3) after a reaction is finished, followed by separation by silica gel column chromatography to obtain the dialdehyde compound.

Optionally, the separation by silica gel column chromatography in step (3) adopts a chloroform/petroleum ether mixture as an eluent; and preferably, the chloroform/petroleum ether mixture includes chloroform and petroleum ether in a volume ratio of 4:1.

Optionally, the dialdehyde compound is in a mole ratio of 1:(5-7) to the dicyanoethyl rhodanine in step (4).

Optionally, the catalyst is added in an amount of 0.4 to 1.0 milliliter per millimole (mL/mmol) of dialdehyde compound in the step (4).

Optionally, the solvent includes but is not limited to chloroform, dichloromethane, toluene, tetrahydrofuran and acetic acid in the step (4).

Optionally, the catalyst in step (4) is at least one selected from a group of pyridine, DBU (1,8-diazabicycloundec-7-ene), piperidine, ammonium acetate and triethylamine, where the DBU is a compound with a molecular formula of $C_9H_{16}N_2$.

Optionally, the reacting in step (4) is carried out under temperature of 20-100° C. for a duration of 0.5-16 h; the temperature can be 20° C., 25° C., 30° C., 35° C., 40° C., 45° C., 50° C., 55° C., 60° C., 65° C., 70° C., 75° C., 80° C., 85° C., 90° C., 95° C., 100° C., etc.; and the duration can be 0.5 h, 1 h, 1.5 h, 2 h, 2.5 h, 3 h, 4 h, 4.5 h, 5 h, 5.5 h, 6 h, 6.5 h, 7 h, 7.5 h, 8 h, 8.5 h, 9 h, 9.5 h, 10 h, 10.5 h, 11 h, 11.5 h, 12 h, 12.5 h, 13 h, 13.5 h, 14 h, 14.5 h, 15 h, 15.5 h, and 16 h, etc.

Optionally, after a reaction is finished in the step (4), the solvent is distilled off from a reaction solution under reduced pressure, followed by separation by silica gel column chromatography to obtain the small-molecule electron donor material.

Optionally, the separation by silica gel column chromatography in step (4) adopts a chloroform/petroleum ether mixture as an eluent; and preferably, the chloroform/petroleum ether mixture includes chloroform and petroleum ether in a volume ratio of 6:1.

As mentioned above, the small-molecule electron donor material with an electron-deficient heterocyclic core, its preparation and application provided by the present application achieve the following beneficial effects:

the small-molecule electron donor material with an electron-deficient heterocyclic core provided by the present application has a skeleton structure of A-D-A'-D-A; it can be used as an electron donor material for all-small-molecule solar cells with good solubility, stability, photoelectric property and solution processability; the small-molecule electron donor material with an electron-deficient heterocyclic core provided by the present application forms a rather excellent phase separation morphology with the small-molecule acceptor material as comparing to traditional small-molecule donor based on benzodithiophene (BDT) core and oligothiophene, and the all-small-molecule organic solar cell prepared by the small-molecule electron donor material provided by the present application provides excellent photoelectric conversion efficiency; and the present application provides a brand-new designing concept of small-molecule donor based on oligothiophene skeleton, which solves the problems of complex synthesis and high cost of BDT core donor materials, and make full use of the advantages of few synthesis routes and low cost of oligothiophene, thus opening up a brand-new and simple synthesis route for the structural design of small-molecule electron donor materials. The present application has great application potential and value in the fields of organic solar cells and related photovoltaics.

DETAILED DESCRIPTION OF THE EMBODIMENTS

The following embodiments of the application are illustrated by specific concrete examples, and other advantages and effects of the present application can be readily understood by those skilled in the art as disclosed herein. The present application may also be implemented or applied by different specific embodiments, and the details in this specification can be modified or changed in various ways without departing from the spirit of the present application, based on different views and applications. It should also be understood that the specific process parameters, etc. of the following embodiments are only one example of a suitable range, i.e., the person skilled in the art can make a suitable selection through the descriptions herein, and are not intended to be limited to the specific values of the examples below.

In the following embodiments, a cathode material is Indium tin oxide (ITO), a hole transport layer is poly(3,4-ethyenedioxythiophene): poly(styrene sulfonate) (pedot: PSS), and an electron acceptor material in an active layer is BTP-eC9-4F; an electron transport layer uses phenyl(2-naphthyl)diphenyl phosphine oxide (Phe-NaDPO), and an anode material is silver (Ag).

Figure 2:
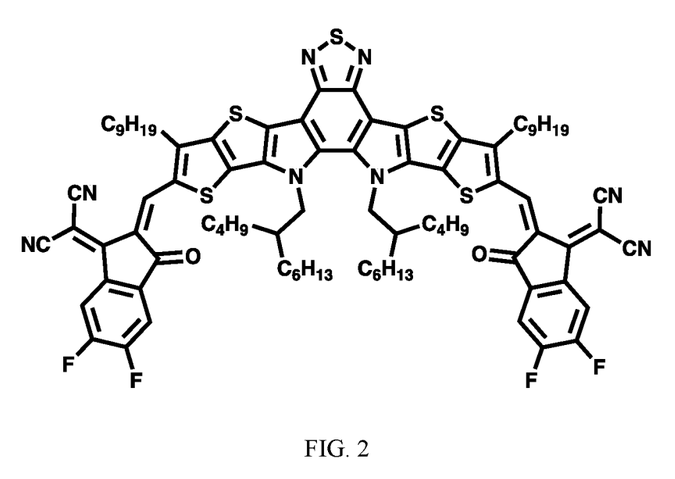
FIG. 2 illustrates molecular structures of electron acceptor material BTP-eC9-4F used in Embodiment 3 and Embodiment 4 of the present application.

The following embodiments adopt ITO purchased from the Youxuan Technology Company, Clevios AL4083 as EDOT:PSS, BTP-eC9-4F from Derthon Optoelectronics Materials Science Technology Co., Ltd. with a structural formula as shown in FIG. 2, and Phe-NaDPO purchased from 1-Material Tech Inc. Other raw materials and reagents that are not indicated by the way of purchase can be purchased from the market.

Embodiment 1

Figure 1:
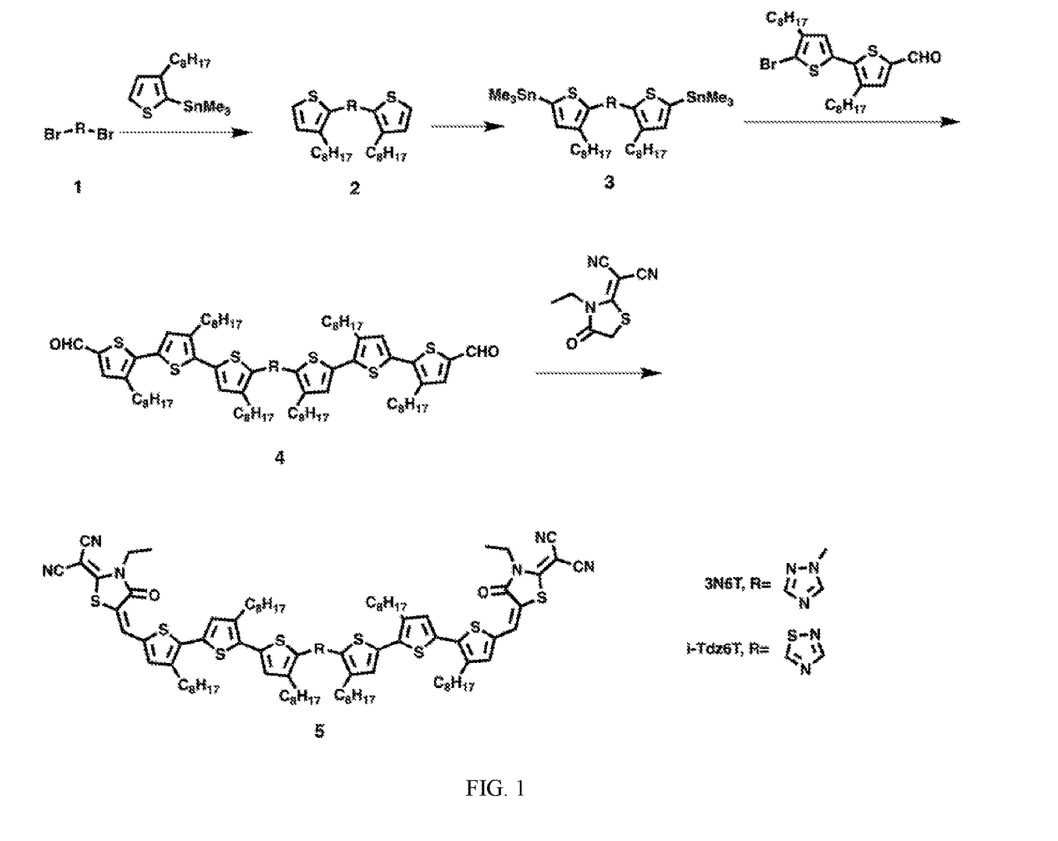
FIG. 1 shows a synthesis route of small-molecule electron donor materials with an electron-deficient heterocyclic core of Embodiments 1 and 2 of the present application.

As shown in FIG. 1, an electron donor material with electron-deficient heterocyclic core in this embodiment is prepared as follows.

1. Synthesis of Compound 2

Compound 1 (1.0 equiv. purchased from Energy) and octylthiophene tin reagent (2.4 equiv. purchased from GR-Chem) are dissolved in 50 milliliters (mL) of anhydrous toluene, and then 150 milligrams (mg) of Pd (PPh3) 4(tetratriphenylphosphine palladium) is added, followed by stirring at 130 degree Celsius (° C.) for reaction of 48 hours (h), then a solvent is removed under reduced pressure, and separation is performed using silica gel column chromatography with a chloroform/petroleum ether mixture (by volume, chloroform:petroleum ether=1:6) as an eluent, then a product (compound 2) of pale yellow oil (with a yield of 65 percent (%) of the theoretical yield).

Characterization data of compound 2: $^1$H NMR (400 MHz, Acetone, δ ppm): 7.72 (d, J=5.2 Hz, 1H), 7.39 (d, J=4.8 Hz, 1H), 7.20 (d, J=5.2 Hz, 1H), 7.04 (d, J=5.2 Hz, 1H), 3.97 (s, 3H), 3.18 (t, J=7.6 Hz, 2H), 2.85-2.81 (m, 3H), 1.73-1.62 (m, 6H), 1.43-1.23 (m, 26H), 0.94-0.85 (m, 9H).

2. Synthesis of Compound 3

Compound 2 (1.0 equiv.) is dissolved in 50 mL tetrahydrofuran in a reaction bottle, and dropwise added with lithium diisopropylamide (2.4 equiv. purchased from Energy) in a low-temperature reactor at −80° C. under nitrogen atmosphere, followed by stirring at low temperature for 1.5 h and dropwise adding with trimethyltin chloride (3.0 equiv. purchased from Energy); then the reaction bottle is moved to room temperature and stirred for 12 h, followed by quenching the reaction with saturated potassium iodide aqueous solution, extracting with ethyl acetate, and drying with anhydrous magnesium sulfate, then the solvent is removed under reduced pressure, and a compound 3 of light brown oil is obtained.

3. Synthesis of Dialdehyde Compounds:

The double tin reagent substitute of the compound 2 (compound 3) (1.0 equiv.) thiophene π-bridged aldehyde (2.4 equiv. ordered from GR-Chem) are dissolved in 50 mL of toluene, then 150 mg of Pd(PPh3) 4(tetratriphenylphosphine palladium) is added, followed by stirring at 130° C. for 48 h; then the solvent is removed under reduced pressure and separated by silica gel column chromatography, where chloroform/petroleum ether (by volume, chloroform:petroleum ether=4:1) is used as the eluent, and a dialdehyde product of reddish brown solid is obtained (with a yield of 80% of the theoretical yield).

Characterization data of dialdehyde compound: $^1$H NMR (400 MHz, CDCl$_3$, δ ppm): 9.83 (s, 1H), 9.82 (s, 1H), 7.60 (s, 1H), 7.58 (s, 1H), 7.14 (s, 1H), 7.13 (s, 1H), 7.10 (s, 1H), 7.04 (s, 1H), 3.99 (s, 2H), 3.75-3.69 (m, 10H), 3.14 (t, J=7.6 Hz, 2H), 2.84-2.74 (m, 10H), 1.72-1.57 (m, 26H), 1.41-1.22 (m, 80H), 0.89-0.83 (m, 18H).

4. Synthesis of Compound 3N6T

Dialdehyde compound (compound 4) (0.200 gram (g), 0.153 millimole (mmol)) and dicyanoethyl rhodanine (0.178 g, 0.921 mmol from GR-Chem) are dissolved in 50 mL chloroform, and then 0.5 mL pyridine is added, followed by reaction under room temperature for 4 h; then the solvent is removed under reduced pressure and separated by silica gel column chromatography, with eluent of chloroform/petroleum ether (by volume, chloroform:petroleum ether=6:1), then a product compound 3 of black solid if obtained (0.220 g, with a yield of 86% of the theoretical yield).

Characterization data of compound 3N6T: $^1$H NMR (400 MHz, CDCl$_3$, δ ppm): 8.00 (s, 1H), 7.99 (s, 1H), 7.30 (s, 1H), 7.29 (s, 1H), 7.19 (s, 1H), 7.18 (s, 1H), 7.13 (s, 1H), 7.07 (s, 1H), 4.35-4.29 (m, 4H), 4.00 (s, 3H), 3.75-3.70 (m, 6H), 3.15 (t, J=7.6 Hz, 2H), 2.88-2.76 (m, 11H), 1.76-1.64 (m, 15H), 1.49-1.22 (m, 95H), 0.89-0.83 (m, 20H).

Embodiment 2

As shown in FIG. 1, an electron donor material with electron-deficient heterocyclic core in this embodiment is prepared as follows.

1. Synthesis of Compound 2

Dihalogenated isothiadiazole (1.0 equiv. purchased from Energy) and octylthiophene tin reagent (2.4 equiv. purchased from GR-Chem) are dissolved in 50 mL of anhydrous toluene,
and then 150 mg of Pd(PPh3) 4(tetratriphenylphosphine palladium) is added, followed by stirring at 130° C. and reaction for 48 h; then the solvent is removed under reduced pressure and separated by silica gel column chromatography, where the chloroform/petroleum ether (by volume, chloroform:petroleum ether=1:6) is used as an eluent, and a product (compound 2) of pale yellow oil is obtained (the yield is 40% of the theoretical yield).

Characterization data of compound 2: $^1$H NMR (400 MHz, CDCl$_3$, δ ppm): 7.45 (d, J=4.8 Hz, 1H), 7.32 (d, J=5.2 Hz, 1H), 7.03 (d, J=5.2 Hz, 1H), 6.99 (d, J=4.8 Hz, 1H), 3.23 (t, J=7.6 Hz, 2H), 2.919 (t, J=7.6 Hz, 2H), 1.76-1.56 (m, 5H), 1.48-1.23 (m, 23H), 0.89-0.85 (m, 7H).

2. Synthesis of Compound 3

Compound 2 (1.0 equiv.) is dissolved in 50 mL tetrahydrofuran in a reaction bottle, and dropwise added with lithium diisopropylamide (purchased by 2.4 equiv. Anergi) in a low-temperature reactor at −80° C. under nitrogen atmosphere, followed by stirring under low temperature for 1.5 h and adding with trimethyltin chloride (3.0 equiv. purchased from Energy); then the reaction bottle is moved to room temperature and stirred for 12 h, and the reaction is quenched with saturated potassium iodide aqueous solution, followed by extraction with ethyl acetate and drying with anhydrous magnesium sulfate, then the solvent is removed under reduced pressure to obtain a compound 3 of light brown oil.

3. Synthesis of Dialdehyde Compounds

The double tin reagent substitute of the compound 2 (compound 3) (1.0 equiv.) and thiophene π-bridged aldehyde (2.4 equiv. ordered from GR-Chem) are dissolved in 50 mL of toluene, and added with 150 mg of Pd(PPh3)4 (tetratriphenylphosphine palladium), followed by stirring at 130° C. and reacting for 48 h; then the solvent is removed under reduced pressure and separated by silica gel column chromatography with eluent of chloroform/petroleum ether (by volume, chloroform:petroleum ether=4:1), and a dialdehyde product of reddish brown solid is obtained (with a yield of 80% of the theoretical yield).

Characterization data of aldehyde compound: $^1$H NMR (400 MHz, CDCl$_3$, δ ppm): 9.88 (s, 2H), 7.20 (s, 1H), 7.16 (s, 1H), 7.10 (s, 1H), 7.08 (s, 1H), 3.21 (t, J=7.6 Hz, 1H), 2.88 (t, J=7.6 Hz, 1H), 2.63-2.58 (m, 2H), 2.54-2.49 (m, 2H), 1.80-1.69 (m, 2H), 1.62-1.23 (m, 38H), 0.90-0.83 (m, 9H).

4. Synthesis of compound i-Tdz6T

Aialdehyde compound (compound 4) (0.200 g, 0.153 mmol) and dicyanoethyl rhodanine (0.178 g, 0.921 mmol from GR-Chem) are dissolved in 50 mL chloroform, then 0.5 mL pyridine is added, followed by stirring and reacting at room temperature for 4 h; then the solvent is removed under reduced pressure and separated by silica gel column chromatography, with eluent of chloroform/petroleum ether (by volume, chloroform:petroleum ether=6:1), and a product compound 3 of black solid (0.220 g, a yield of 86% of the theoretical yield) is obtained.

Characterization data of compound i-Tdz6T: $^1$H NMR (400 MHz, CDCl$_3$, δ ppm): 7.95 (s, 2H), 7.28 (s, 2H), 7.15 (s, 1H), 7.10 (s, 1H), 7.04 (s, 1H), 7.02 (s, 1H), 4.32 (m, 4H), 3.14 (t, J=7.6 Hz, 2H), 2.81 (t, J=7.6 Hz, 2H), 2.57-2.46 (m, 9H), 1.73-1.62 (m, 5H), 1.56-1.17 (m, 885H), 0.83-0.76 (m, 20H).

Embodiment 3

An all-small-molecule organic solar cell is prepared by using the small-molecule electron donor material with an electron-deficient heterocyclic core prepared in Embodiment 1 (i.e. 3N6T shown in FIG. 1). The specific preparation process is as follows:

substrate composed of transparent glass and transparent conductive electrode ITO is subjected to ultrasonic cleaning with cleaning solution, deionized water, acetone and isopropanol respectively, and blow-drying with nitrogen after cleaning; then the substrate is treated in an ozone cleaner for 15 minutes (min), and spin-coated with a hole transport layer material PEDOT:PSS (4,000 revolutions per minute (rpm) for 20 second (s) with a film thickness of 30 nanometers (nm)), followed by thermal annealing (120° C., 10 min) in the air; then the sample is sent into a glove box filled with nitrogen to prepare an active layer (3N6T:BTP-eC9-4F=2:1, 40 mg/mL, with film thickness of the active layer of about 200 nm) on the PEDOT:PSS hole transport layer by spin coating method, and the prepared active layer film is subjected to annealing treatment (CF, 30 s) in a solvent in glove box; then, an electron transport layer DPO (2,000 rpm, 10 s, film thickness 8 nm) is spin-coated on the active layer, and then an Ag electrode (film thickness of 100 nm) is vapor-deposited onto the electron transport layer, and a solar cell is prepared.

Embodiment 4

Figure 3:
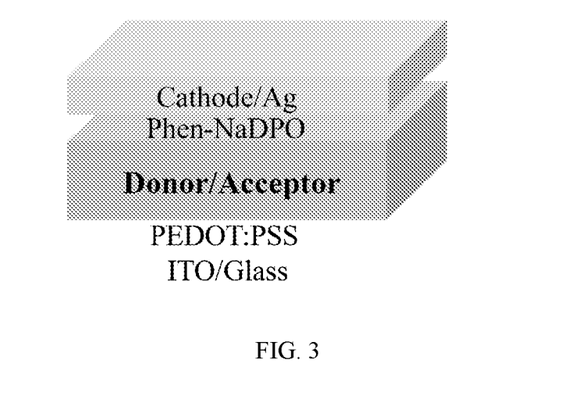
FIG. 3 is a schematic diagram illustrating structures of all-molecule organic solar cell devices in Embodiment 3 and Embodiment 4 of the present application.

An all-small-molecule organic solar cell is prepared by using the small-molecule electron donor material with an electron-deficient heterocyclic core prepared in Embodiment 1 (i.e. i-Tdz6T as shown in FIG. 1), with specific preparation process as follows:

substrate composed of transparent glass and transparent conductive electrode ITO is subjected to ultrasonic cleaning with cleaning solution, deionized water, acetone and isopropanol respectively, and blow-drying with nitrogen after cleaning; then the substrate is treated in an ozone cleaner for 15 min, and spin-coated with a hole transport layer material PEDOT:PSS (4,000 rpm for 20 s with a film thickness of 30 nm), followed by thermal annealing (120° C., 10 min) in the air; then the sample is sent into a glove box filled with nitrogen to prepare an active layer (i-Tdz6T:BTP-eC9-4F=2:1, 40 mg/mL, active layer film thickness of about 200 nm) on the PEDOT:PSS hole transport layer by spin coating method, and the prepared active layer film is subjected to annealing treatment (CF, 30 s) in a solvent in glove box; then, an electron transport layer DPO (2,000 rpm, 10 s, film thickness 8 nm) is spin-coated on the active layer, and then an Ag electrode (film thickness of 100 nm) is vapor-deposited onto the electron transport layer, and a solar cell is prepared; the solar cells prepared in Embodiments 3-4 are illustrated in FIG. 3 in terms of structure.

Figure 4:
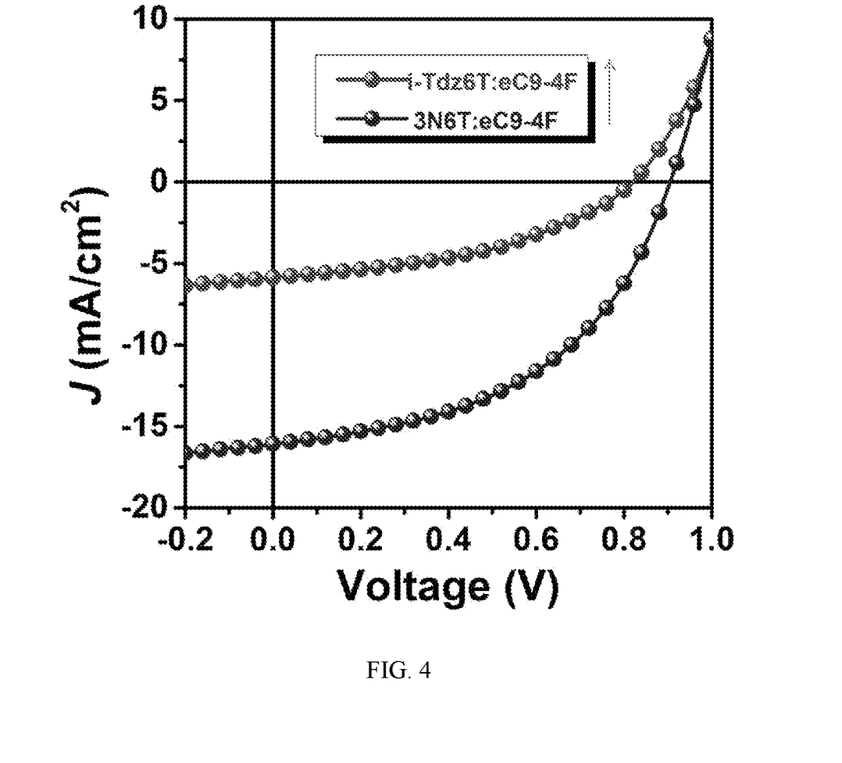
FIG. 4 shows current density-voltage characteristic curves of devices in Embodiment 3 (3N6T:BTP-eC9-4F=2:1 40 milligrams per milliliter (mg/mL)) and Embodiment 4 (I-TDZ6T: BTP-EC9-4F=2:1 40 mg/mL) of the present application under standard test conditions (AM1.5, 100 milliwatts per square centimeter (mW/cm$^2$)).

The optical J-V curves of the organic solar cells obtained in Embodiment 3 and Embodiment 4 are shown in FIG. 4, and the optical J-V PV performance parameters are shown in Table 1.

TABLE 1

| Condition | $V_{oc}$ (V) | $J_{sc}$ (mA/cm2) | FF (%) | PCE (%) |
|---|---|---|---|---|
| Embodiment 3 | SVA = CF/30s | 0.905 | 16.08 | 48.92 | 7.12 (6.92 ± 0.09) |
| Embodiment 4 | SVA = CF/30s | 0.821 | 5.86 | 43.12 | 2.07 (2.01 ± 0.12) |

In Table 1, SVA represents solvent annealing, $V_{oc}$ is voltage, $J_{sc}$ represents short-circuit current density, FF stands for filling factor, and PCE is short for photoelectric conversion efficiency.

As can be seen from Table 1, when chloroform is used as the solvent and annealing duration is 30 s, the photoelectric conversion efficiency of organic solar cell with 3N6T as the active layer with methyltriazole as the core is obviously excellent; the small-molecule electron donor material with isothiadiazole as the core has a lower efficiency due to the absence of methyl twist, but it also works properly and has the potential to be optimized, which suggest that the design scheme proposed in the present application for preparing small-molecule electron donor materials with electron-deficient heterocycles as the core is of universal applicability.

In summary, the small-molecule electron donor material with electron-deficient heterocyclic core provided by the present invention has excellent repeatability and solution processability, and achieves relatively good photoelectric conversion efficiency compared with traditional benzodithiophene (BDT)-based, oligothiophene small-molecule electron donor material, and still achieves relatively good photoelectric conversion efficiency after changing the core electron-deficient unit, demonstrating good universality; and the active layer film has a thickness of up to 200 nm, which is applicable to spin-coating and printing processes of all-small-molecule organic solar cells, and, of course, is not limited to organic solar cells, but also applicable to other photovoltaic devices.

The above embodiments are merely illustrative of the principles of the application and its effectiveness, and are not intended to limit the application. Any person skilled in the art may modify or change the above embodiments without violating the spirit and scope of the present application. Therefore, all equivalent modifications or alterations made by a person with ordinary knowledge in the art, for example, without departing from the spirit and technical ideas revealed by the present application, shall still be covered by the claims of the present application.

What is claimed is:

1. A small-molecule electron donor material with an electron-deficient heterocyclic core, comprising a molecular structure shown in formula (I):

wherein R is any one of following structures:

2. The small-molecule electron donor material with an electron-deficient heterocyclic core according to claim 1, wherein the molecular structure is:

3. An active layer material for photovoltaic device, comprising the small-molecule electron donor material with an electron-deficient heterocyclic core according to claim 1.

4. The active layer material according to claim 3, wherein the active layer material also comprises an electron acceptor material.

5. The active layer material according to claim 4, wherein the electron acceptor material comprises at least one selected from a group of $PC_{71}BM$, Y6, BTP-eC9-4F, CH1007, IDIC, and N3.

6. A method for preparing the small-molecule electron donor material with an electron-deficient heterocyclic core according to claim 1, comprising: mixing raw materials and reacting to obtain the small-molecule electron donor material with an electron-deficient heterocyclic core; wherein the raw materials comprise dialdehyde compound and dicyanoethyl rhodanine, and the dialdehyde compound has a molecular structural formula as follows:

wherein R is any one of following structures

7. The method according to claim 6, wherein the method comprises:
 (1) mixing dibromo electron-deficient heterocyclic unit, solvent, octylthiophene tin reagent and catalyst, and reacting to obtain a compound 2;
 (2) mixing the compound 2 with solvent and lithium diisopropylamide, reacting, adding alkyl tin chloride reagent for reaction so as to obtain a compound 3;
 (3) mixing the compound 3 with solvent, thiophene π-bridged aldehyde and catalyst, reacting to obtain a dialdehyde compound; and
 (4) mixing the dialdehyde compound with solvent, dicyanoethyl rhodanine and catalyst, and reacting to obtain the small-molecule electron donor material, wherein a reaction route is as follows:

-continued

8. The method according to claim 7, wherein:
the dibromo electron-deficient heterocyclic unit is in a mole ratio of 1:(2.0-2.5) to the octylthiophene tin reagent;
and, the dibromo electron-deficient heterocyclic unit is in a mole ratio of 1:(0.1-0.2) to the catalyst;
and, the solvent in the step (1) comprises at least one selected from a group of dioxane, toluene, chlorobenzene and o-xylene;
and, the catalyst in the step (1) is at least one selected from a group of tetrakis (triphenylphosphine)palladium, tris (dibenzylideneacetone) dipalladium, and [1,1'-bis (diphenylphosphino) ferrocene] dichloropalladium (II);
and, the reacting in the step (1) is carried out under temperature of 100-200 degree Celsius (° C.) for a duration of 12-72 hours (h);
and, the solvent is distilled off from a reaction solution under reduced pressure in the step (1) after the reaction is finished, followed by separation by silica gel column chromatography to obtain the compound 2;
and, the compound 2 is in a mole ratio of 1:(2.0-3.0) to lithium diisopropylamide in the step (2);
and, the compound 2 is in a mole ratio of 1:(3.0-5.0) to alkyl tin chloride reagent in the step (2); and the solvent comprises at least one selected from a group of tetrahydrofuran, 2-methyltetrahydrofuran, ether and toluene in the step (2);
and, the alkyl tin chloride reagent in the step (2) is any one selected from a group of trimethyltin chloride, triethyltin chloride, trinpropyltinchloride, chlorotributyltin and chloro(trioctyl)stannane;
and, the compound 2 and lithium diisopropylamide in the step (2) are reacted at a temperature of −30° C.--100° C. for a duration of 0.5-2.5 h; and, in the step (2), the reaction under room temperature is carried out for a duration of 3-20 h; and, in the step (2), after the reaction is finished, the reaction is quenched, followed by extraction and drying, then the solvent is distilled off from a reaction solution under reduced pressure to obtain the compound 3; and, the compound 3 is in a mole ratio of 1:(2.0-2.5) to the thiophene π-bridged aldehyde in the step (3);
and, the compound 3 is in a mole ratio of 1:(0.1-0.2) to the catalyst in the step (3);
and, the solvent in the step (3) comprises at least one of dioxane, toluene, chlorobenzene and o-xylene;
and, the catalyst in the step (3) is at least one selected from a group of tetrakis (triphenylphosphine)palladium, tris (dibenzylideneacetone) dipalladium, and [1,1'-bis (diphenylphosphino) ferrocene] dichloropalladium (II);
and, the reacting in step (3) is carried out under temperature of 100-200° C. for a duration of 12-72 h;
and, the solvent is distilled off from a reaction solution under reduced pressure in step (3) after a reaction is finished, followed by separation by silica gel column chromatography to obtain the dialdehyde compound;
and, the dialdehyde compound is in a mole ratio of 1:(5-7) to the dicyanoethyl rhodanine in step (4);
and, the catalyst is added in an amount of 0.4 to 1.0 milliliter per millimole (mL/mmol) of dialdehyde compound in the step (4);
and, the solvent in the step (4) comprises at least one selected from a group of chloroform, dichloromethane, toluene, tetrahydrofuran and acetic acid;
and, the catalyst in step (4) is at least one selected from a group of pyridine, DBU (1,8-diazabicycloundec-7-ene), piperidine, ammonium acetate and triethylamine;
and, the reacting in step (4) is carried out under temperature of 20-100° C. for a duration of 0.5-16 h;
and, after a reaction is finished in the step (4), the solvent is distilled off from a reaction solution under reduced pressure, followed by separation by silica gel column chromatography to obtain the small-molecule electron donor material.

* * * * *